(12) United States Patent
Blust

(10) Patent No.: US 9,175,723 B2
(45) Date of Patent: Nov. 3, 2015

(54) SURGICAL INSTRUMENT, SURGICAL HANDPIECE AND SURGICAL DRIVE SYSTEM

(75) Inventor: Edgar Blust, Koenigsfeld (DE)

(73) Assignee: Aesculap AG, Tuttlingen (DE)

( * ) Notice: Subject to any disclaimer, the term of this patent is extended or adjusted under 35 U.S.C. 154(b) by 841 days.

(21) Appl. No.: 13/457,984

(22) Filed: Apr. 27, 2012

(65) Prior Publication Data
US 2012/0283706 A1 Nov. 8, 2012

(30) Foreign Application Priority Data

May 6, 2011 (DE) .......................... 10 2011 050 193

(51) Int. Cl.
A61B 17/00 (2006.01)
F16C 19/46 (2006.01)
F16C 19/49 (2006.01)
F16C 33/46 (2006.01)
A61B 17/16 (2006.01)

(52) U.S. Cl.
CPC ............. *F16C 19/46* (2013.01); *A61B 17/1613* (2013.01); *F16C 19/49* (2013.01); *F16C 33/4605* (2013.01); *F16C 33/4652* (2013.01)

(58) Field of Classification Search
CPC ................ A61B 17/00234; A61B 2017/00367
USPC ...................... 384/548–589; 606/1
See application file for complete search history.

(56) References Cited

U.S. PATENT DOCUMENTS

| 1,169,469 | A | | 1/1916 | Dunning | |
|---|---|---|---|---|---|
| 1,420,852 | A | * | 6/1922 | Lofstrom | 384/561 |
| 1,986,274 | A | * | 1/1935 | Whitmer | 384/552 |
| 2,542,693 | A | * | 2/1951 | McGlinchey | 433/126 |
| 2,855,671 | A | | 10/1958 | Lundgren et al. | |
| 3,980,359 | A | * | 9/1976 | Wetherbee, Jr. | 384/470 |
| 4,820,062 | A | * | 4/1989 | Shirane | 384/486 |
| 4,955,732 | A | * | 9/1990 | Behrens | 384/484 |
| 6,425,690 | B1 | * | 7/2002 | DeWachter | 384/583 |
| 8,292,512 | B2 | * | 10/2012 | Tanaka et al. | 384/531 |
| 2008/0171302 | A1 | | 7/2008 | Kuhn | |
| 2008/0219611 | A1 | * | 9/2008 | Ootsuka et al. | 384/470 |

FOREIGN PATENT DOCUMENTS

| CH | 296826 | 5/1954 |
|---|---|---|
| DE | 915 760 | 7/1954 |
| DE | 1 019 872 | 11/1957 |

(Continued)

OTHER PUBLICATIONS

European Search Report for EP12166169 dated Aug. 17, 2012, 2 pages.

*Primary Examiner* — William Thomson
*Assistant Examiner* — John R Downey
(74) *Attorney, Agent, or Firm* — Lipsitz & McAllister, LLC

(57) ABSTRACT

In order to improve a surgical instrument comprising a shank and a drive shaft, which is rotatably mounted in the shank and bears or comprises a tool element at its distal end, wherein in the distal end region of the shank a radial bearing is arranged or configured for the rotatable mounting of the drive shaft on the shank, such that a reliable operation is possible even with increasing miniaturisation of the shanks, it is proposed that the radial bearing is configured in the form of a needle bearing.

An improved surgical handpiece as well as an improved surgical drive system are additionally proposed.

23 Claims, 17 Drawing Sheets

(56) References Cited

FOREIGN PATENT DOCUMENTS

| | | |
|---|---|---|
| DE | 1 055 752 | 4/1959 |
| DE | 1 898 225 | 8/1964 |
| DE | 1 189 229 | 3/1965 |
| DE | 1 215 446 | 4/1966 |
| DE | 10 2006 010 881 | 9/2006 |
| DE | 10 2006 020 412 | 11/2007 |
| DE | 10 2006 044 802 | 3/2008 |
| DE | 202011050062 | 9/2011 |
| EP | 1 876 365 | 1/2008 |
| GB | 567556 | 2/1945 |

* cited by examiner

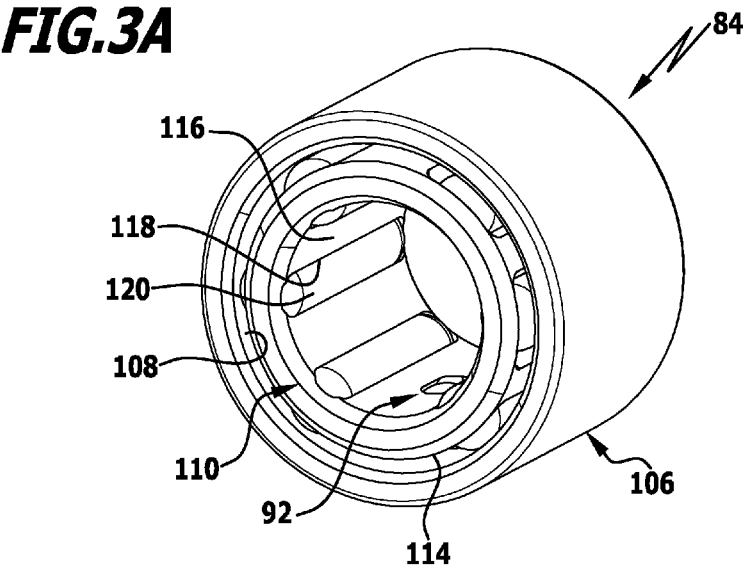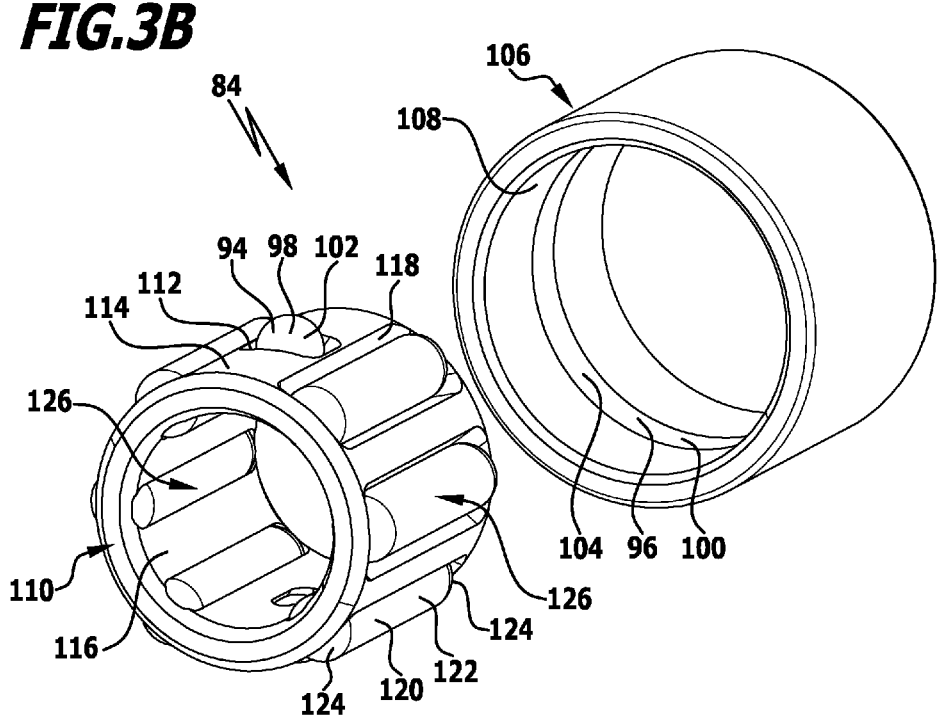

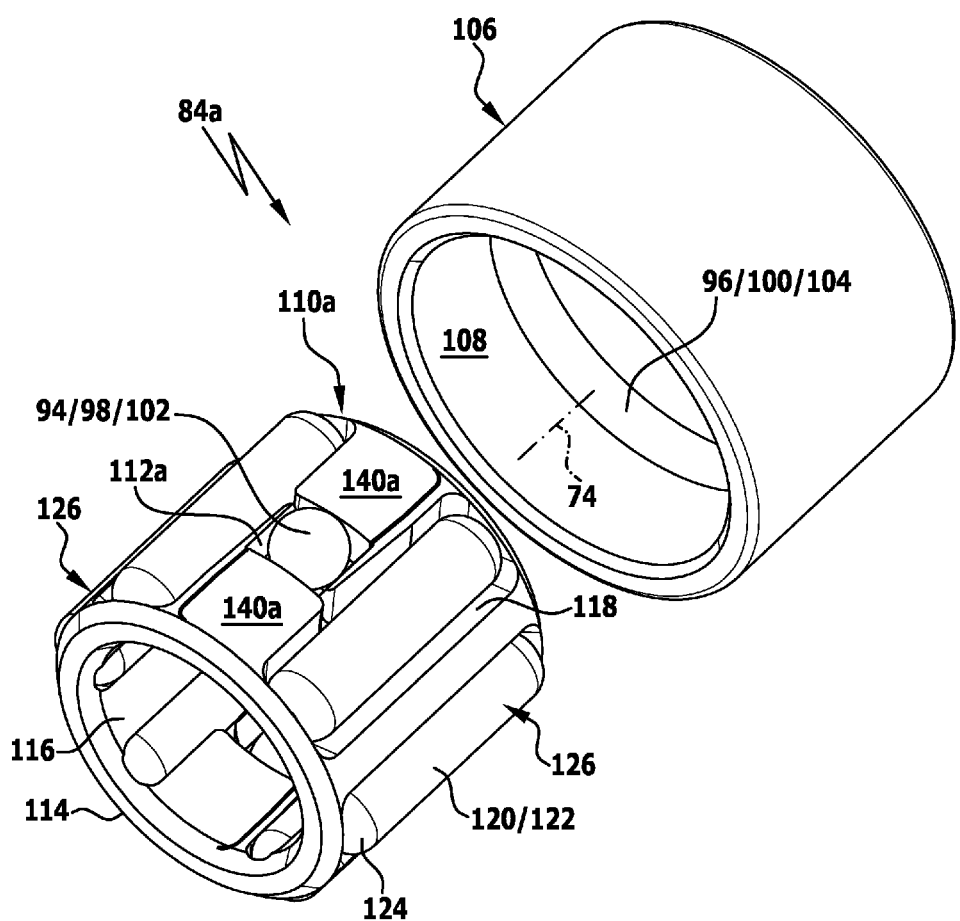

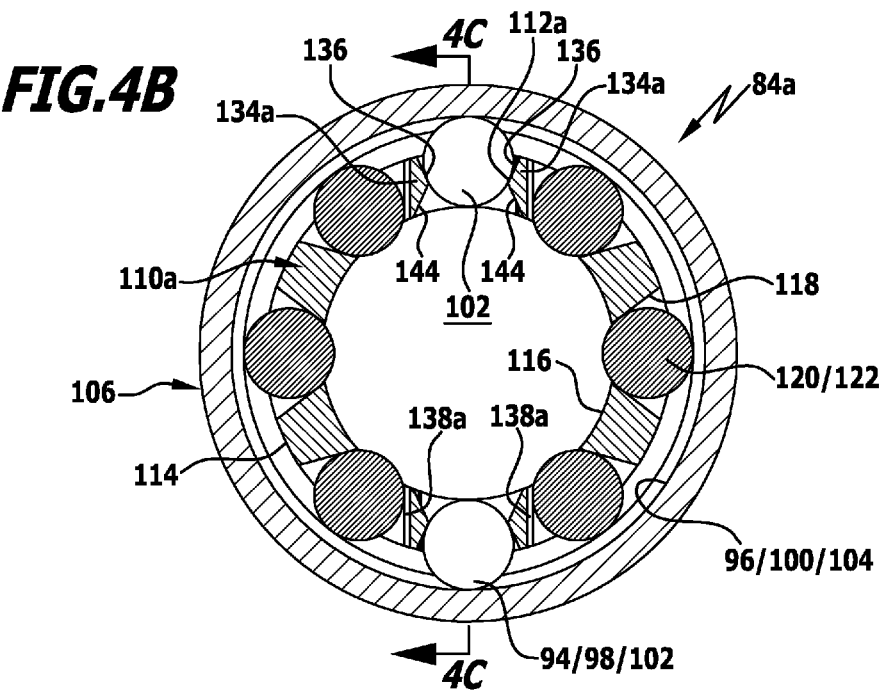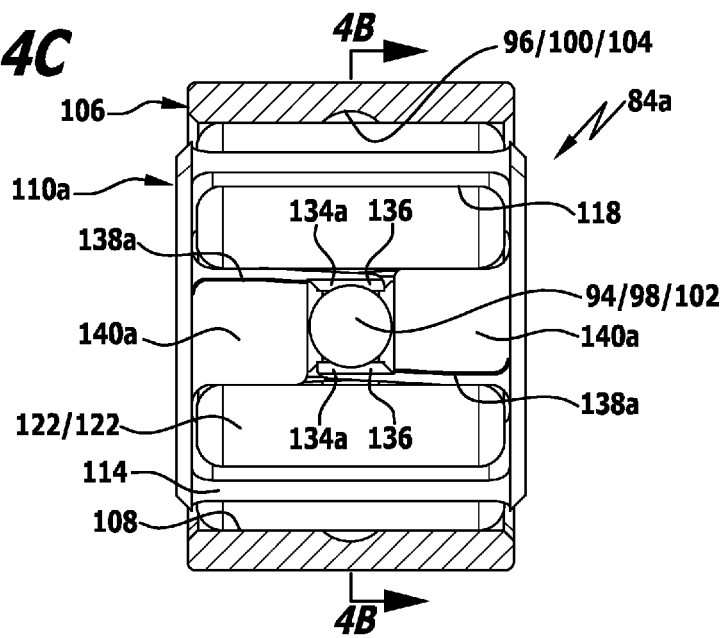

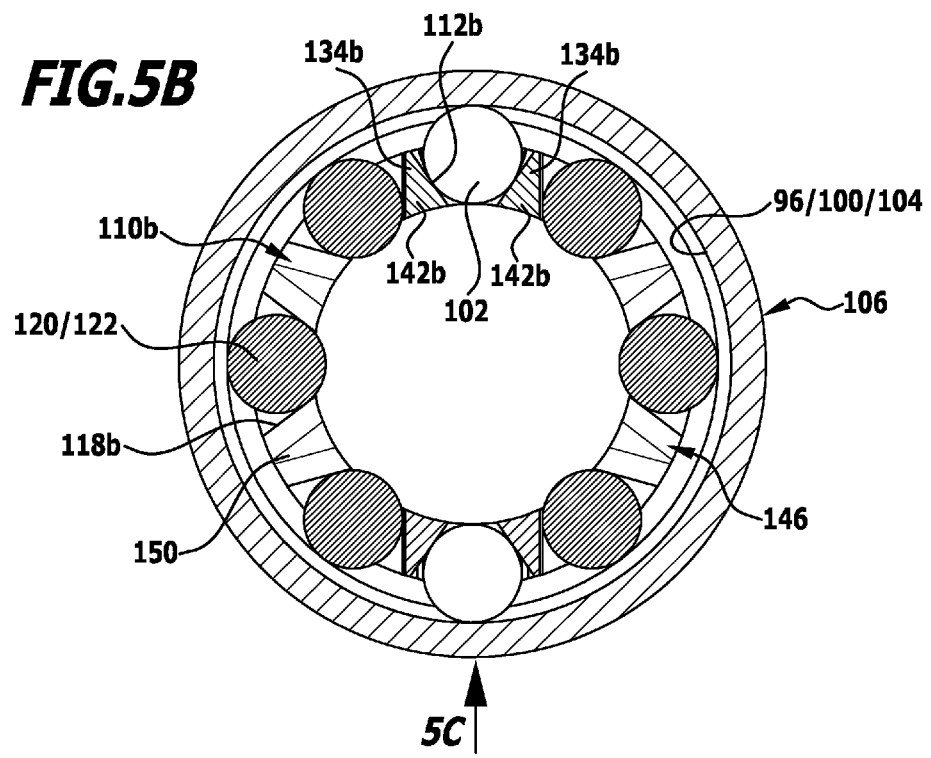
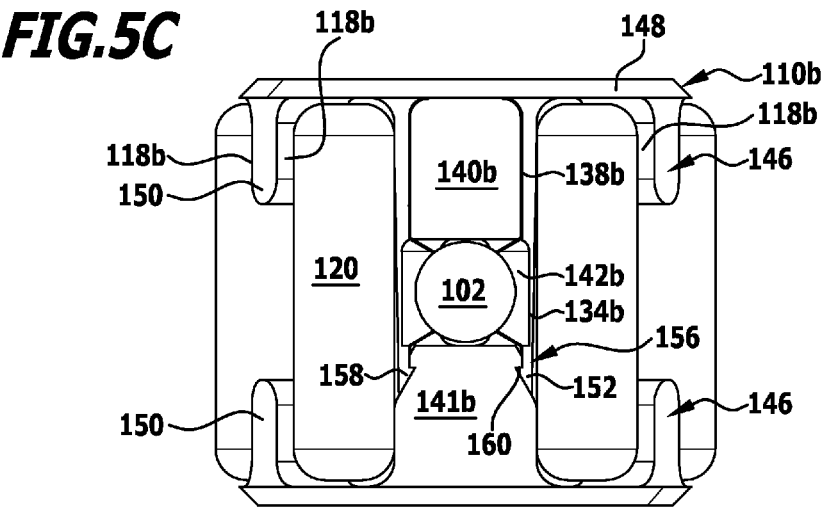

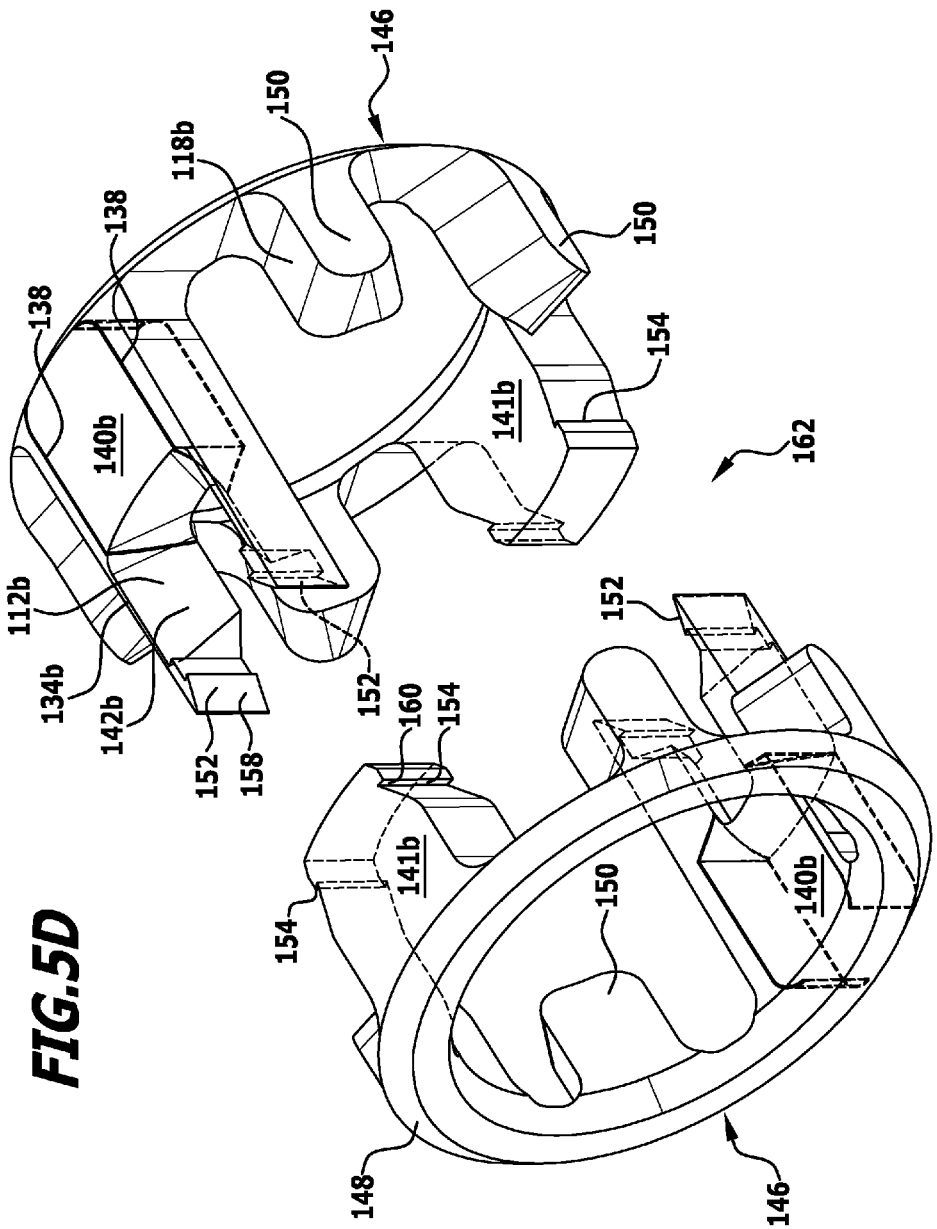

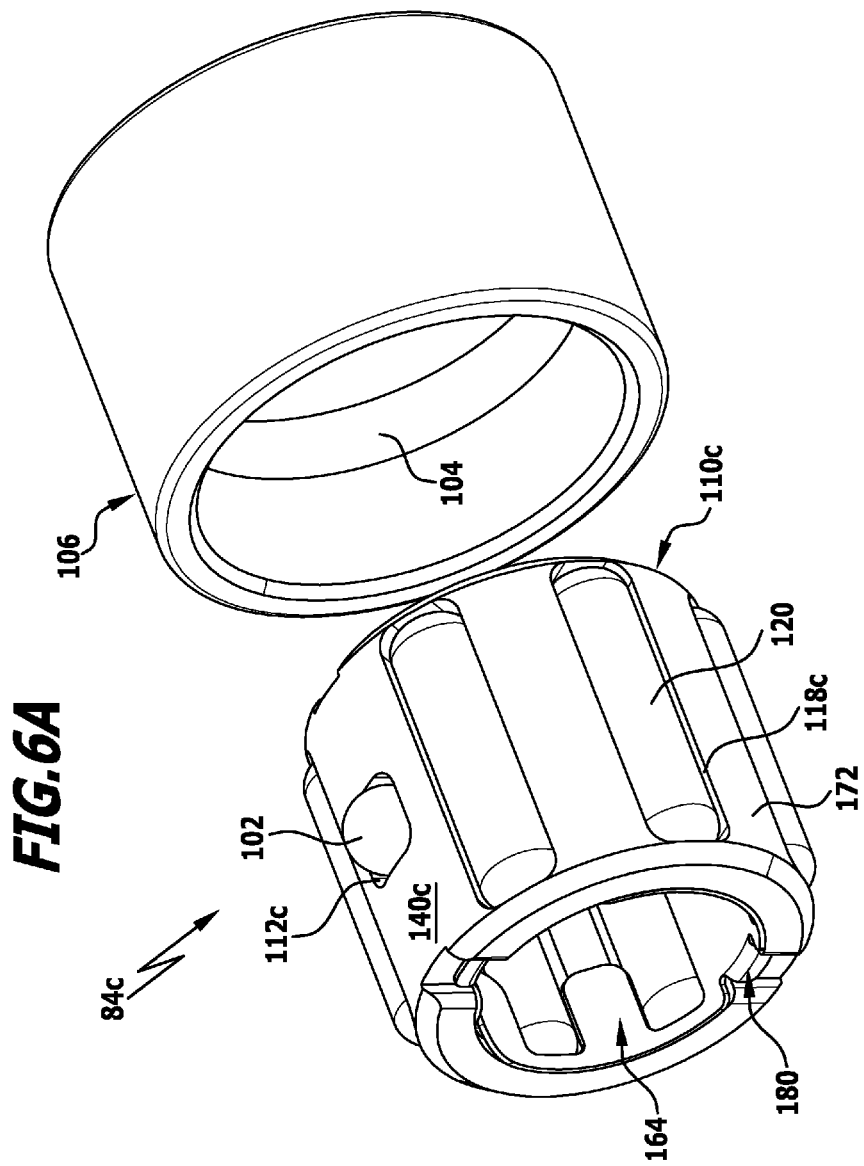

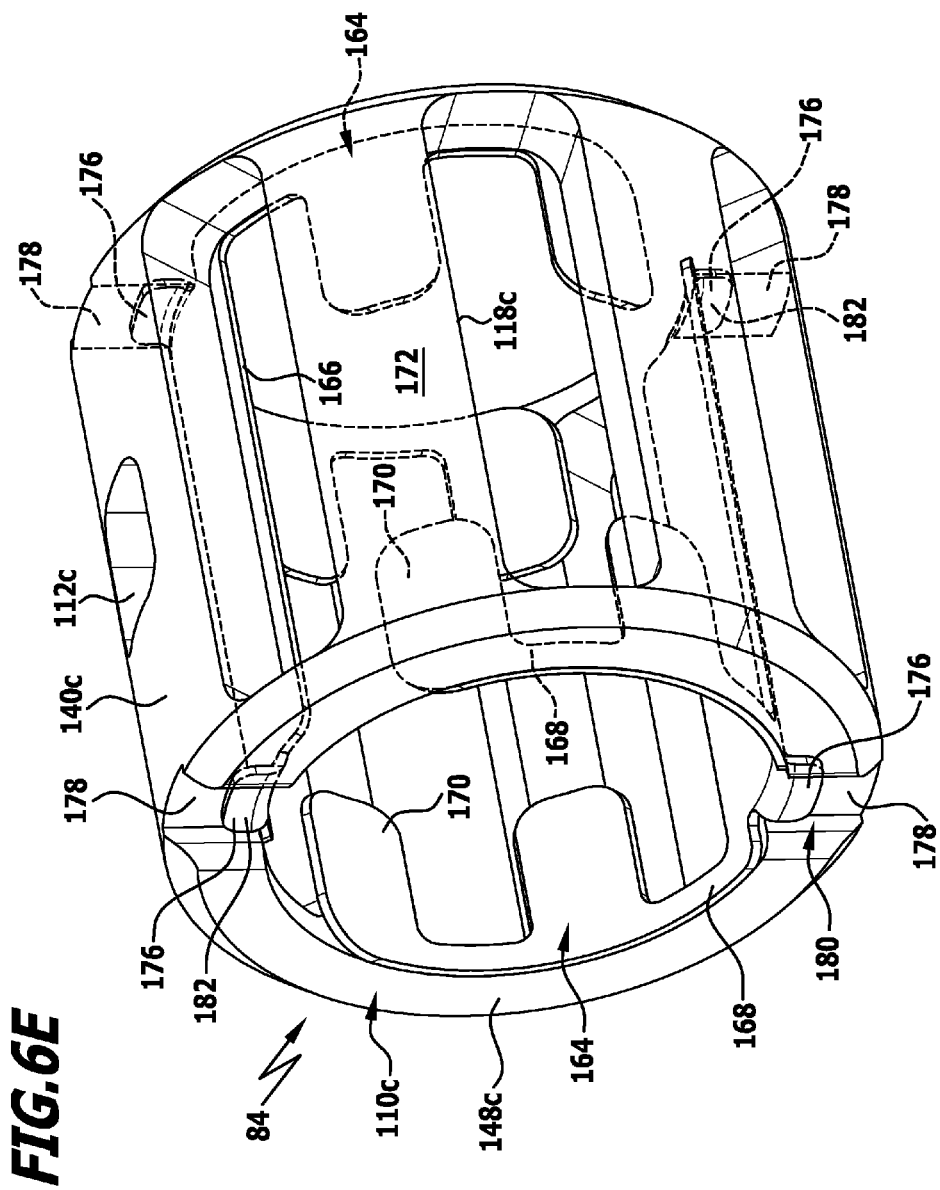

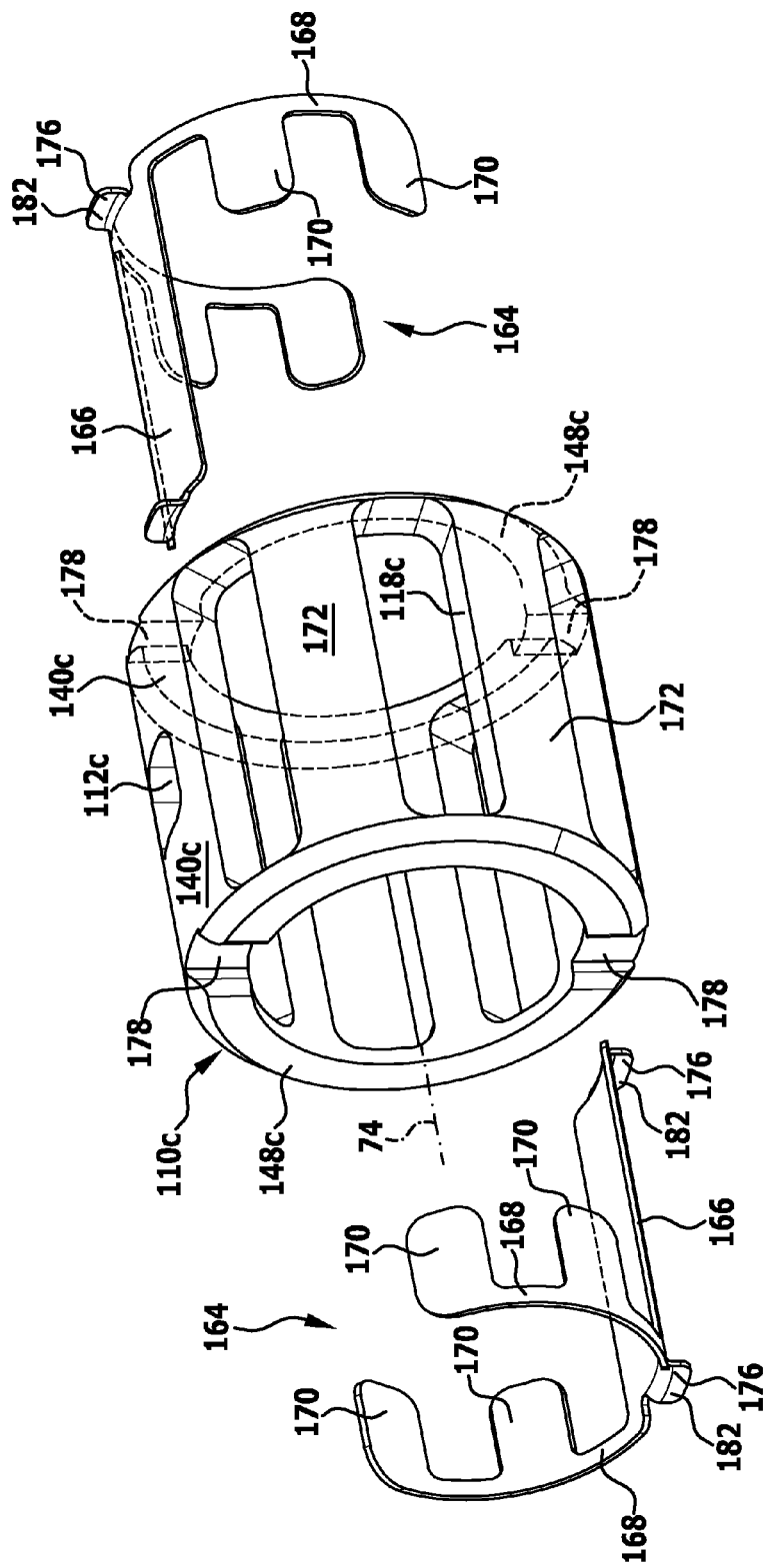

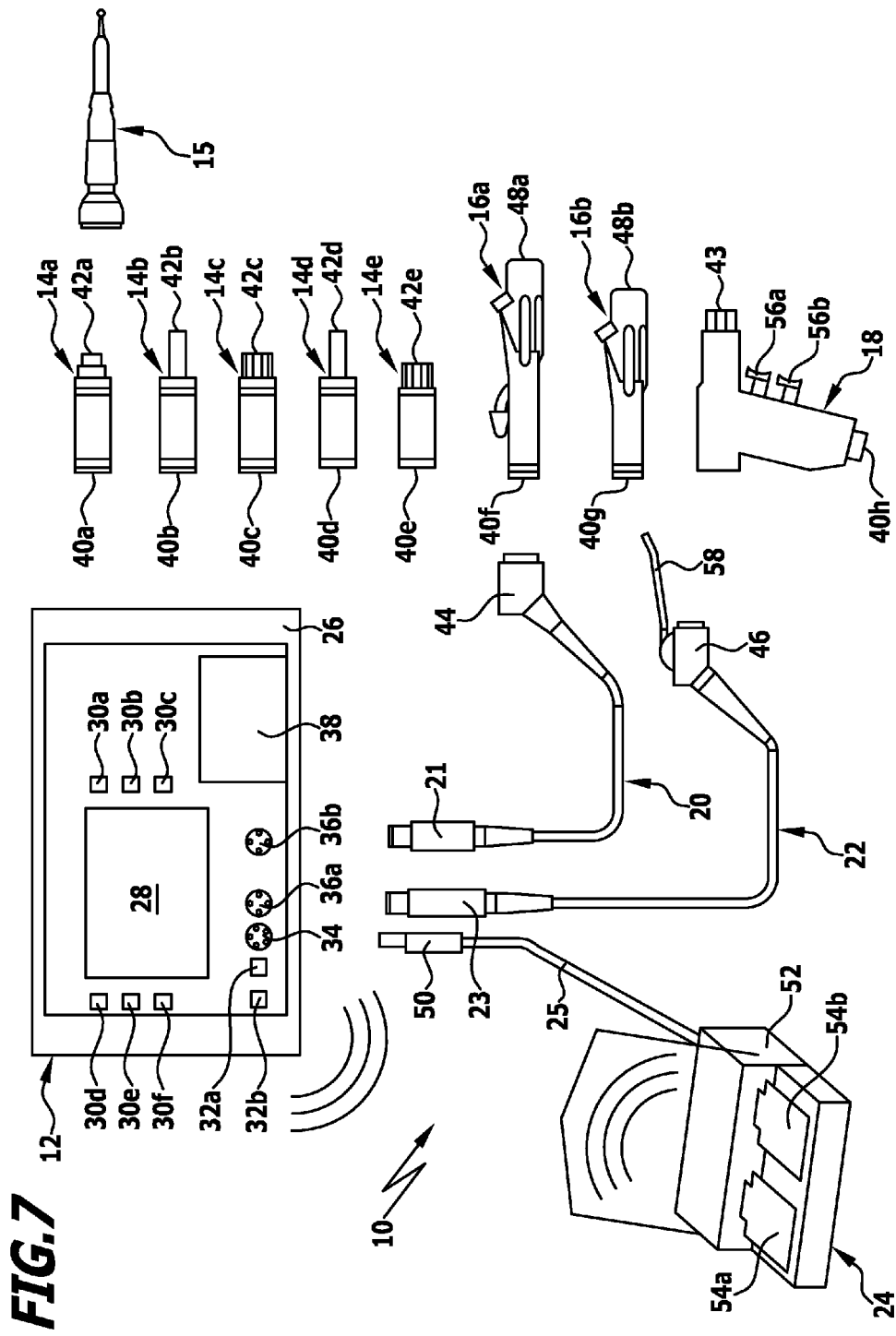

1

SURGICAL INSTRUMENT, SURGICAL HANDPIECE AND SURGICAL DRIVE SYSTEM

CROSS-REFERENCE TO RELATED APPLICATIONS

This application claims the benefit of German Patent Application No. 10 2011 050 193.2 filed on May 6, 2011.

The present disclosure relates to the subject matter disclosed in German patent application number 10 2011 050 193.2, filed May 6, 2011, which is incorporated by reference herein in its entirety and for all purposes.

FIELD OF THE INVENTION

The present invention relates to surgical instruments generally, and more specifically to a surgical instrument comprising a shank and a drive shaft, which is rotatably mounted in the shank and bears or comprises a tool element at its distal end, wherein in the distal end region of the shank a radial bearing is arranged or configured for the rotatable mounting of the drive shaft on the shank.

The present invention additionally relates to surgical handpieces generally, and more specifically to a surgical handpiece comprising a drive arranged in a housing.

And finally, the invention relates to surgical drive systems generally, and more specifically to a surgical drive system comprising at least one surgical handpiece with a drive arranged in a housing and an open-loop and/or closed-loop control device for open-loop and/or closed-loop control of the drive.

BACKGROUND OF THE INVENTION

Surgical instruments of the above-described type are used in particular in surgery. They are coupled to handpieces that include drives in order to set the drive shaft in rotation. A problem with such instruments is the mounting of the drive shaft. This lies, on the one hand, in an increasing miniaturisation of the systems that leads to a reduction of an outside diameter of the shanks of the instruments. It is known to use radial bearings in the form of ball bearings for mounting the shanks. However, these cannot be configured as small as desired. On the other hand, it must be considered that such instruments are operated at very high rotational speeds of up to 100,000 revolutions per minute. Problems related to wear and increased rise in temperature are associated with this.

Therefore, it would be desirable to provide a surgical instrument, a surgical handpiece and also a surgical drive system of the above-described type which allow a reliable operation even with increasing miniaturisation of the shanks.

SUMMARY OF THE INVENTION

In a first aspect of the invention, a surgical instrument comprises a shank and a drive shaft, which is rotatably mounted in the shank and bears or comprises a tool element at its distal end. In the distal end region of the shank a radial bearing is arranged or configured for the rotatable mounting of the drive shaft on the shank. The radial bearing is configured in the form of a needle bearing.

In a second aspect of the invention, a surgical handpiece comprises a drive arranged in a housing and a surgical instrument. Said surgical instrument comprises a shank and a drive shaft, which is rotatably mounted in the shank and bears or comprises a tool element at its distal end. In the distal end region of the shank a radial bearing is arranged or configured for the rotatable mounting of the drive shaft on the shank. The radial bearing is configured in the form of a needle bearing.

In a third aspect of the invention, a surgical drive system comprises at least one surgical handpiece with a drive arranged in a housing and at least one of an open-loop and closed-loop control device for at least one of open-loop and closed-loop control of the drive. The system further comprises at least one surgical instrument. Said at least one surgical instrument comprises a shank and a drive shaft, which is rotatably mounted in the shank and bears or comprises a tool element at its distal end. In the distal end region of the shank a radial bearing is arranged or configured for the rotatable mounting of the drive shaft on the shank. The radial bearing is configured in the form of a needle bearing.

BRIEF DESCRIPTION OF THE DRAWING FIGURES

The foregoing summary and the following description may be better understood in conjunction with the drawing figures, of which:

FIG. 3A is a perspective view of a first exemplary embodiment of the radial bearing shown in FIG. 2;

FIG. 3B is an exploded representation of the arrangement shown in FIG. 3A;

FIG. 4A is an exploded representation of a second exemplary embodiment of a radial bearing;

FIG. 4B is a sectional view taken along line 4B-4B in FIG. 4C;

FIG. 4C is a sectional view taken along line 4C-4C in FIG. 4B;

FIG. 5B is a cross-sectional view of the arrangement shown in FIG. 5A;

FIG. 5C is a side view of the arrangement shown in FIG. 5B in the direction of the arrow 5C;

FIG. 5D is a partially open exploded representation of the bearing cage of the arrangement shown in FIG. 5A in the separation position;

FIG. 6A is an exploded representation of a fourth exemplary embodiment of a radial bearing;

FIG. 6E is a partially open perspective view of the bearing cage of the arrangement shown in FIG. 6A;

FIG. 6F is a partially open exploded representation of the bearing cage shown in FIG. 6E; and FIG. 7 is a schematic general view of a surgical drive system.

DETAILED DESCRIPTION OF THE INVENTION

Figure 1:
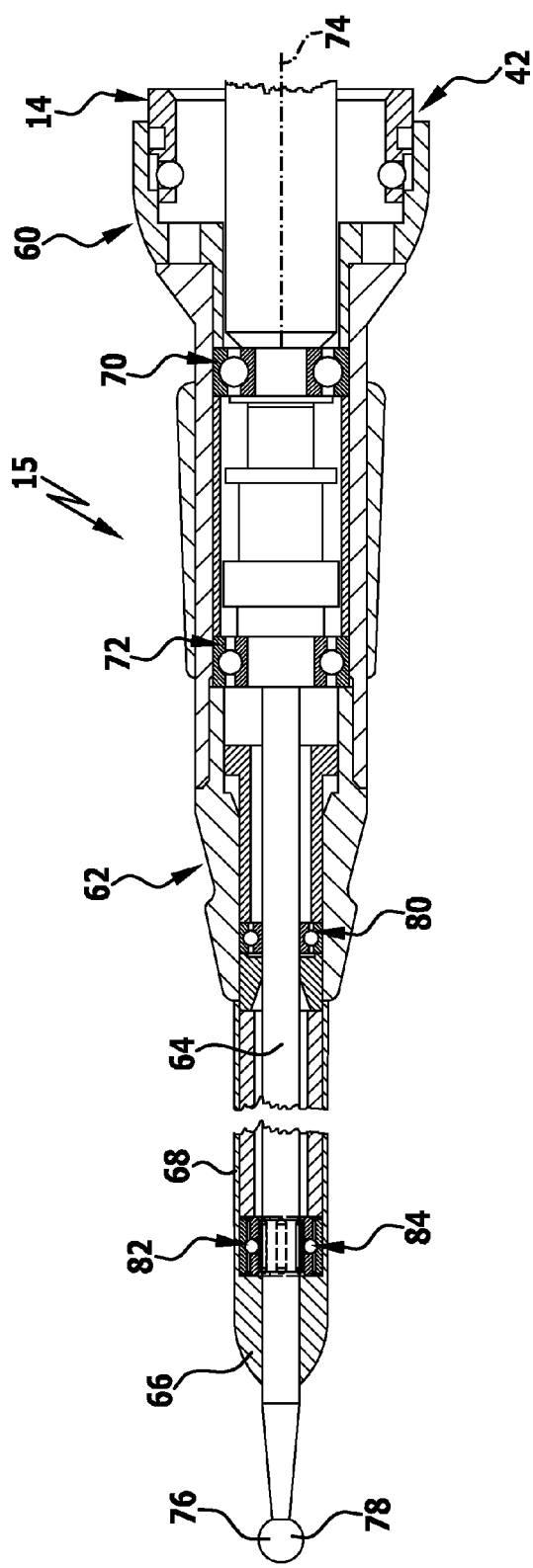
FIG. 1 is a schematic view in longitudinal section of a surgical instrument coupled to a surgical handpiece.
Figure 2:
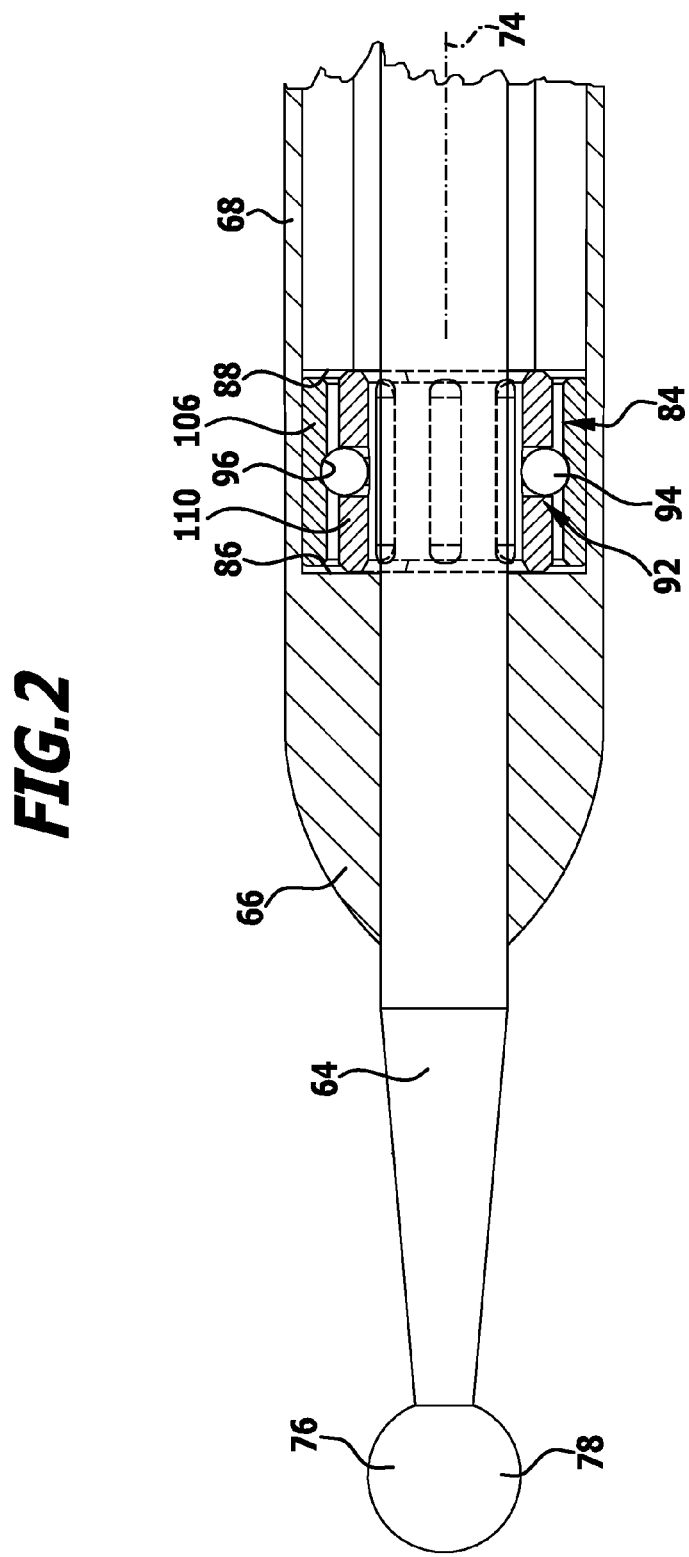
FIG. 2 is an enlarged view of a distal end region of the instrument from FIG. 1.
Figure 3C:
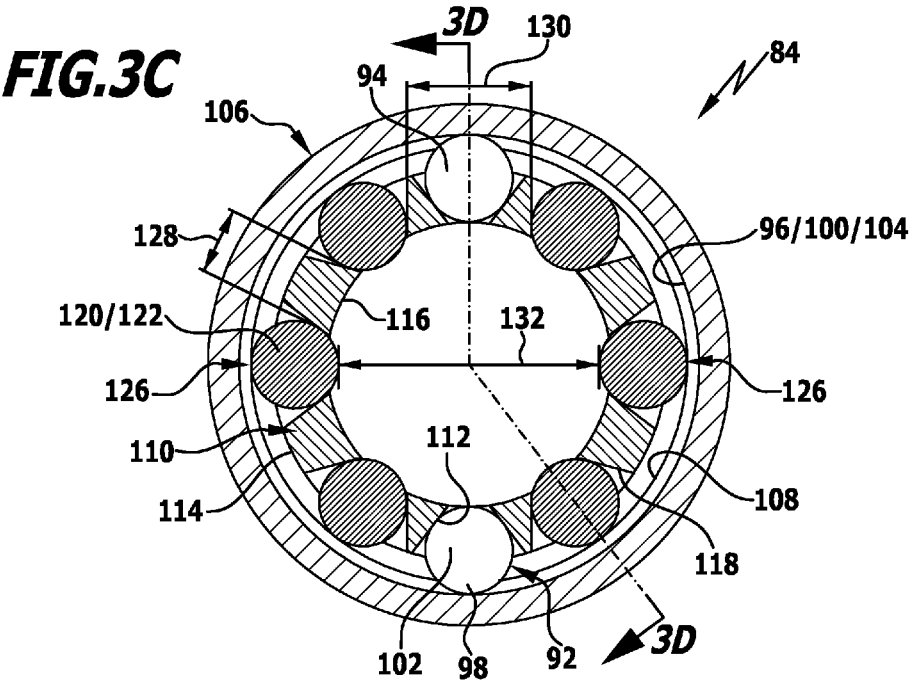
FIG. 3C is a cross-sectional view of the arrangement shown in FIG. 3A.
Figure 3D:
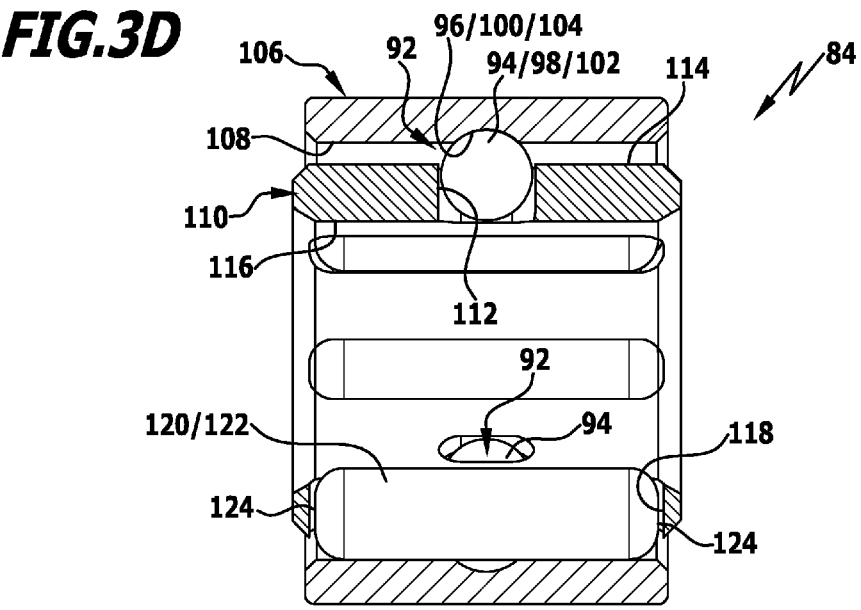
FIG. 3D is a sectional view taken along line 3D-3D in FIG. 3C.
Figure 4D:
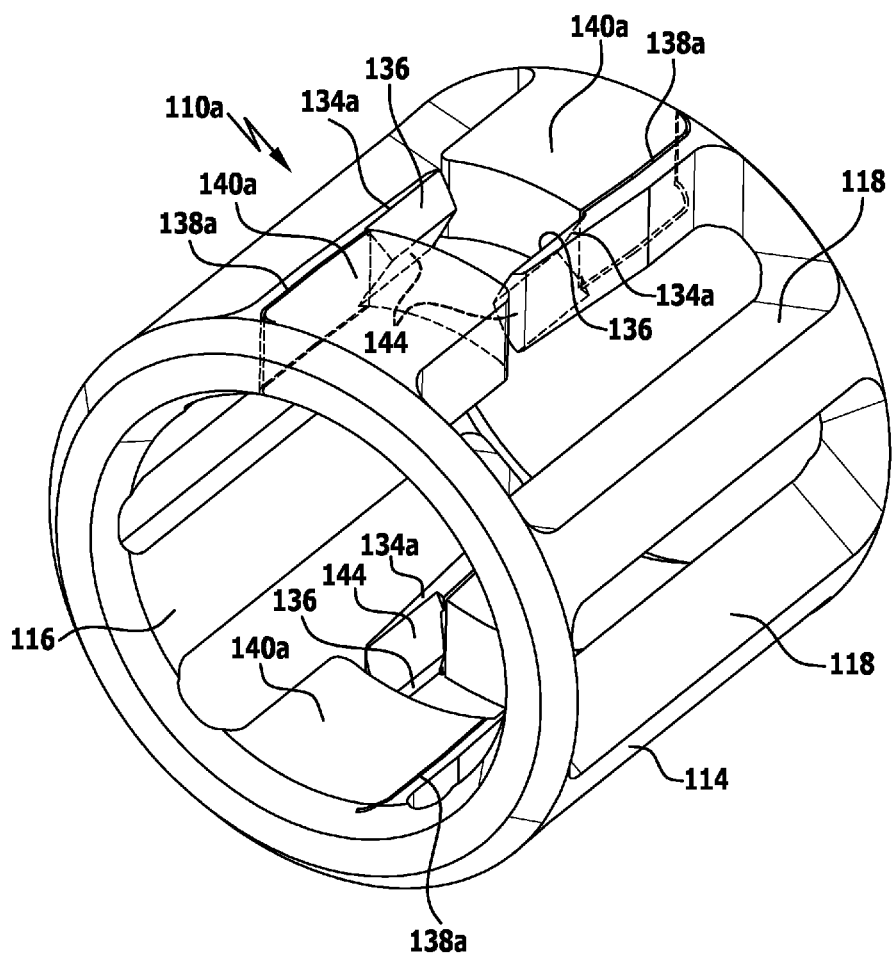
FIG. 4D is a perspective view of the bearing cage of the arrangement shown in FIG. 4A.
Figure 5A:
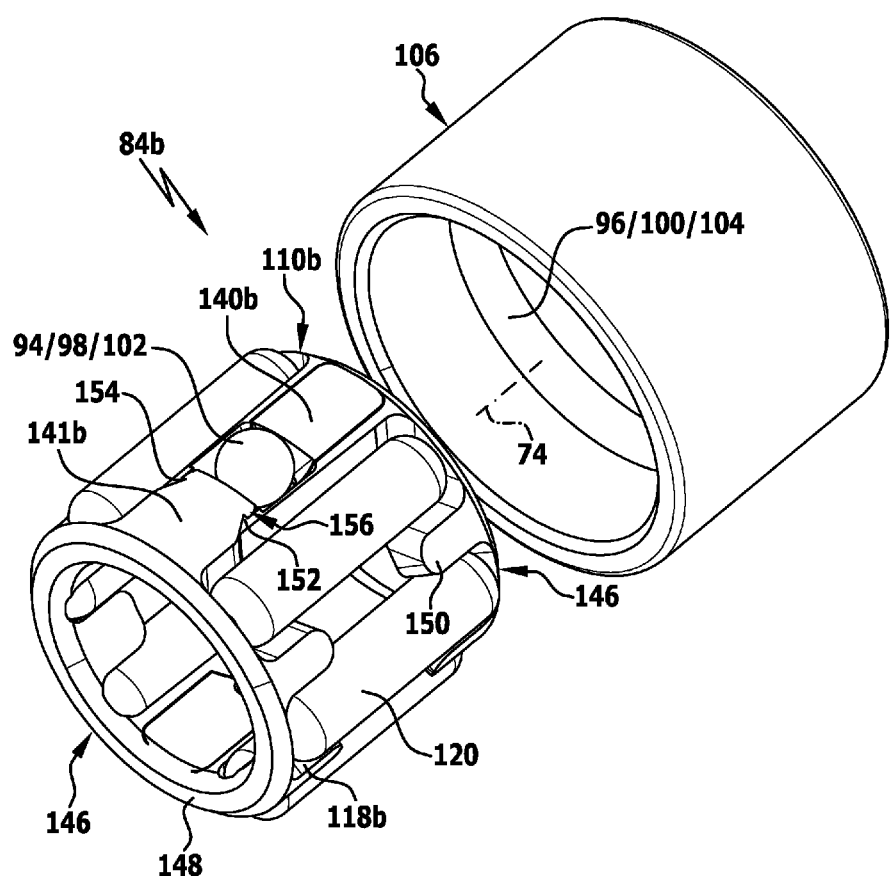
FIG. 5A is an exploded representation of a third exemplary embodiment of a radial bearing.
Figure 5E:
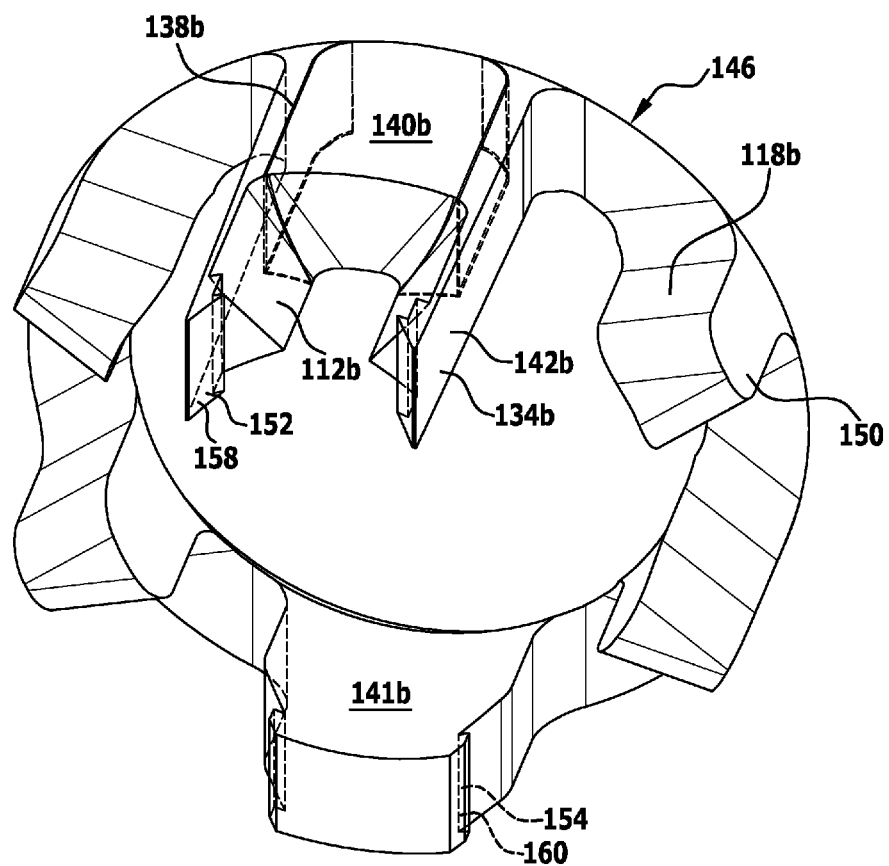
FIG. 5E is an enlarged partially open representation of one of the two identical bearing cage parts shown in FIG. 5D.
Figure 6B:
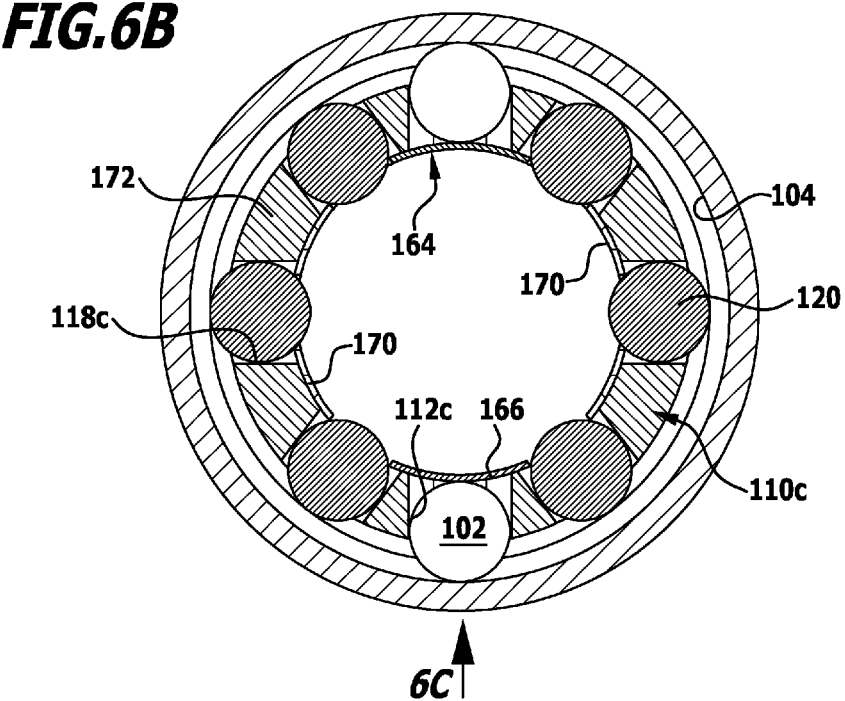
FIG. 6B is a sectional view taken along line 6B-6B in FIG. 6C.
Figure 6C:
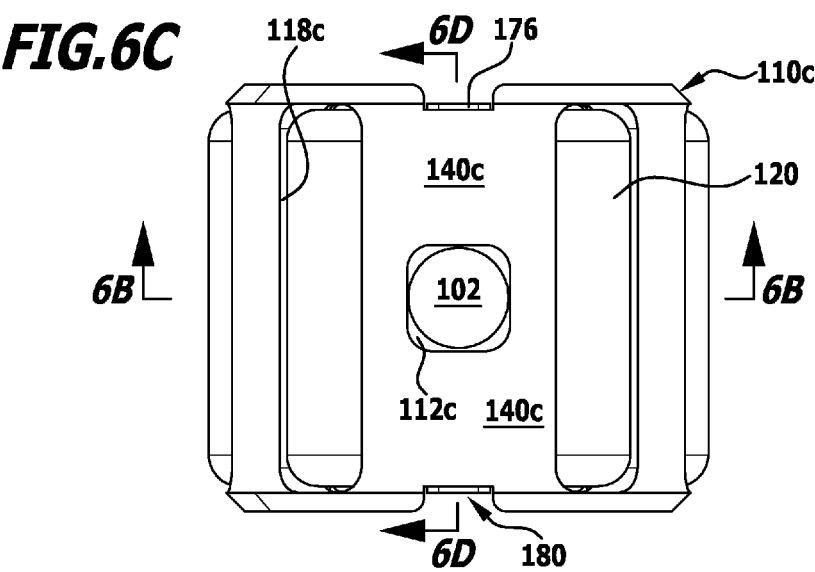
FIG. 6C is a side view of the arrangement shown in FIG. 6B in the direction of the arrow 6C.
Figure 6D:
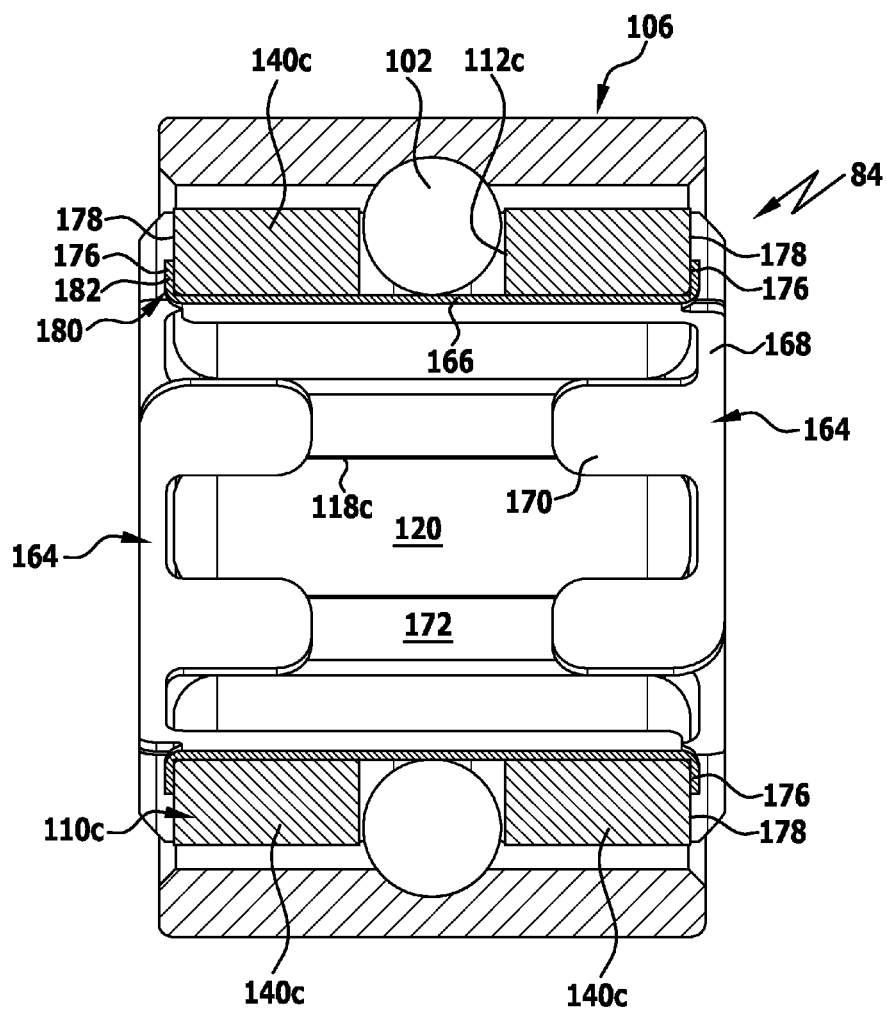
FIG. 6D is a sectional view taken along line 6D-6D in FIG. 6C.

Although the invention is illustrated and described herein with reference to specific embodiments, the invention is not intended to be limited to the details shown. Rather, various modifications may be made in the details within the scope and range of equivalents of the claims and without departing from the invention.

Needle bearings have a significantly higher load capacity compared to ball bearings and can therefore absorb significantly higher forces without being damaged thereby. The needle bearing preferably forms the distal-most radial bearing on the shank, which does not have to absorb any axial forces. Needle bearings cannot absorb any axial forces and therefore needle bearings are excellently suited as radial bearings at this location of the shank. Overall, with the same size, i.e. the same outside diameter, needle bearings can absorb significantly higher forces than ball bearings. In other words, the same forces can be absorbed with needle bearings that have a significantly smaller outside diameter compared to ball bearings.

To simplify assembly of the instrument in particular, it is advantageous if the needle bearing comprises a bearing cage, in which a plurality of bearing needles are rotatably mounted parallel to a longitudinal axis of the needle bearing. The needle bearing can preferably be configured such that it has no inner bearing ring, preferably secured non-rotatably and axially to the drive shaft, but such that the bearing needles can abut directly against the drive shaft and can roll thereon. In this way, a size of the needle bearing and thus also an outside diameter of the shank in particular can be further reduced.

Advantageously the needle bearing comprises at least three bearing needles. With these in particular a 3-point support can be configured for the drive shaft and, moreover, with the smallest possible size.

In order to increase stability of the needle bearing, it is advantageous if at least two bearing needles define a needle group and if the needle bearing comprises at least two needle groups. For example, a needle bearing can thus be configured with at least four bearing needles, which are arranged in pairs to form a needle group. Also conceivable, for example, are two needle groups with three bearing needles or three needle groups respectively with two or three bearing needles.

In addition, it can be advantageous if a spacing of adjacent needle groups from one another in peripheral direction is greater than a spacing of adjacent bearing needles of a needle group from one another in peripheral direction. In other words, needle groups can thus be spatially separated from one another in peripheral direction. A larger spacing allows, for example, further elements to be provided on the bearing cage between the needle groups that axially secure the bearing cage on the shank, for example.

Advantageously, the needle bearing is held axially secured on the shank. In this way, it can be prevented from moving relative to the shank in a direction parallel to a longitudinal axis of the drive shaft.

According to a preferred embodiment of the invention it can be provided that the instrument comprises a needle bearing locking arrangement for axially securing the needle bearing on the shank. Thus, the needle bearing can be secured against an axial movement relative to the shank in a simple manner.

It is particularly favourable if the needle bearing locking arrangement comprises at least one first locking element and at least one second locking element, if one of the at least one first and second locking elements is arranged or held on the needle bearing, if the other of the at least one first and second locking elements is arranged or held on the shank, and if the at least one first locking element and the at least one second locking element are in engagement with one another in a locking position. In this way, the needle bearing locking arrangement can be configured in a particularly simple and compact manner. In particular, assembly requirements can thus also be considered individually with respect to design to simplify the assembly of the instrument.

It is advantageous if the bearing cage defines a longitudinal axis and comprises an inner surface concentrically surrounding the longitudinal axis and an outer surface concentrically surrounding the longitudinal axis and if the at least one first locking element protrudes from the outer surface or projects beyond the outer surface, but not however over the inner surface. In this way, it can be prevented that the at least one first locking element comes into contact with the drive shaft. It can thus be ensured that the at least one first locking element serves exclusively for the axial securing of the needle bearing and cannot overheat by friction at the drive shaft. Moreover, an exchange of the drive shaft is thus enabled in a simple manner. This is particularly desirable if the tool element is undetachably connected to the drive shaft, and in particular formed in one piece therewith. The at least one first locking element can be configured, for example, in the form of a ball defining a locking projection, the ball extending into an annular groove of the shaft or of a sleeve held thereon or a bearing ring held thereon, and thus locks the bearing cage axially on the shaft.

It is favourable if the at least one first locking element is configured in the form of a locking projection, if the at least one second locking element is configured in the form of a locking recess, and if the locking projection and the locking recess are in engagement with one another in the locking position. In particular, both the locking projection and the locking recess can be oriented in a direction transverse to a longitudinal axis defined by the needle bearing to thus obtain an axial locking of the needle bearing on the shank in an optimum manner.

Preferably, the locking projection is configured in the form of a ball and the locking recess in the form of an annular groove corresponding to the ball. The use of balls as locking projections has the advantage in particular that wear and also temperature increase can be reduced here in relation to simple lateral stops at very high rotational speeds in the range of 80 000 revolutions per minute to 100 000 revolutions per minute. Moreover, an assembly of the bearing cage on the shank can thus also be simplified. Both the bearing needles and the balls are preferably held in corresponding recesses on the bearing cage. Advantageously, these are conically shaped in order to prevent both the bearing needles and the balls from falling out of the bearing cage in the direction of the longitudinal axis.

It is particularly favourable if the annular groove is open towards the longitudinal axis of the needle bearing. Thus, the balls protruding or projecting from the bearing cage as radial locking projections can engage into the annular groove and axially secure the needle bearing on the shank.

It would also be conceivable in principle to form the locking recess directly on the shank. However, it is favourable if the locking recess is formed on a holding ring, which is secured axially to the shank to be fixed against rotation. Such a configuration simplifies the production of the instrument, since it is significantly simpler to produce an annular groove provided in an inside wall on a holding ring than on an elongated shank. Moreover, the holding ring can also be made of a different material from the shank, as a result of which stability can be specifically increased and wear can be reduced in accordance with the choice of materials. In particular, the holding ring can be held pressed into the shank, i.e. held with a press fit, or can be held on the shank between two stops acting in axial direction.

It is advantageous if a locking projection is arranged or configured on the bearing cage between two bearing needles. Thus, for example, a radial bearing can be configured to the inside by the bearing needles, on the one hand, while to the outside the needle bearing can be secured on the shank by means of the locking projection. If the locking projection is configured in the form of a ball, a corresponding recess or depression can be provided on the bearing cage. In this case, this does not necessarily have to be a through opening, since the holding ring is preferably configured in such a manner that the ball cannot fall out to the outside. For example, three bearing needles can thus form a three-point support for the drive shaft and three locking projections can form a three-point support for holding the bearing cage on the shank.

Moreover, it can also be favourable if a locking projection is arranged or configured on the bearing cage between two needle groups. In this way, the number of contact lines defined by the bearing needles on the drive shaft can be increased in the desired manner, which results in a further increase in a load capacity of the needle bearing.

In order to assure that the needle bearing is secured on the shank as securely as possible, it is advantageous if at least two locking projections are provided. These are then arranged or held ideally offset 180° on the bearing cage. In the case of three locking projections a uniform distribution thereof over the periphery of the bearing cage is likewise obtained, so that in the case of three locking projections a 120° separation is favourable.

It is advantageous if the instrument comprises at least two first and/or second locking elements arranged offset in the longitudinal direction of the needle bearing. Such an arrangement can improve an axial locking of the needle bearing on the shank. For example, two pairs each of two locking elements axially offset relative to one another can be arranged or configured axially offset 180° in peripheral direction on the bearing cage.

To obtain as high a loading capacity of the needle bearing as possible, it is favourable if the number of bearing needles corresponds to an integral multiple of the number of the first or second locking elements. For example, two locking elements in the form of balls and four bearing needles, which respectively form a needle group comprising two bearing needles, can be provided. It is also conceivable to provide a total of six or eight bearing needles, which are grouped in groups of two or three bearing needles.

To be able to simplify work on the bones and tissue of patients, it is favourable if the distal end of the drive shaft protrudes out of the distal end of the shank. For example, a milling cutter can thus be configured with a milling tool or cutter head, which forms the distal end of the drive shaft or is arranged or held thereon.

The most optimum mounting possible of the drive shaft can be achieved in particular by a minimum inside diameter of the needle bearing delimited by the bearing needles corresponding to an outside diameter of the drive shaft.

The assembly of the instrument can be simplified in particular by the bearing cage being formed in one piece.

Advantageously, the bearing cage is made from an at least partially elastic material. It can thus be elastically deformed for assembly in such a way that it can be inserted into the above-described holding ring, for example. After insertion of the bearing cage into the holding ring, this can then return to its original shape and, for example, can be axially secured on the shank by means of a locking projection in the form of a ball. In particular, it can already be fitted with the bearing needles and, if necessary, locking elements in the form of balls upon insertion into the holding ring.

It is favourable if for each first locking element the bearing cage comprises a locking element seating, in which the locking element is held with a holding member. Such a configuration enables the first locking elements to be attached to or mounted on the bearing cage in a simple manner. For example, the first locking element can be configured in the form of a ball, which is then held by means of the holding member in a corresponding seating, which in particular can be conically shaped.

The insertion of the first locking element into the locking element seating can be simplified in particular by the holding member being movable from an assembly position, in which the first locking element can be inserted into the locking element seating, into a locking position in which the first locking element is undetachably held on the bearing cage. Thus, the first locking element, for example, can be inserted into the locking element seating in the assembly position and is then undetachably held on the bearing cage in the locking position. In particular, it is advantageous if the holding member is configured to be elastically resilient. For example, the first locking element can thus be inserted into the locking element seating, wherein during insertion the holding member can pivot out of the locking position into the assembly position and after final insertion of the first locking element into the locking element seating can pivot back into the starting position again and can undetachably hold the first locking element on the bearing cage.

The production of the instrument becomes particularly simple if the holding member is configured in the form of a holding web or a holding arm.

The assembly of the instrument can be further simplified in particular by the bearing cage comprising two interconnected bearing cage parts. For example, the bearing needles and also corresponding locking elements, e.g. balls, can thus be mounted on the bearing cage in a simple manner. For example, they can be inserted into one of the two bearing cage parts and then secured undetachably on the bearing cage with the second bearing cage part upon connection thereof to the first bearing cage part.

Both the design and the assembly of the instrument can be further simplified in particular by
the bearing cage being configured from two identical bearing cage parts.

The instrument preferably comprises a connection device for connecting the two bearing cage parts. In particular, the connection device enables the bearing cage parts to be connected undetachably to one another.

The bearing cage parts can be connected to one another particularly simply and quickly if the connection device is configured in the form of a snap-in locking arrangement. In other words, the bearing cage parts can thus be brought into engagement with one another and lock together in a connection position.

It is favourable if the connection device comprises first and second connection elements, which are respectively arranged or configured on one of the two bearing cage parts, which first and second connection elements are disengaged in a separation position and are in engagement with one another in a connection position. Such a connection device can be simply produced and allows a simple and secure assembly of the bearing cage.

A first and a second connection element respectively delimit a locking element seating preferably at least partially. The first and second connection elements can thus perform a dual function. On the one hand, they can partially delimit the locking element seating to thus hold a locking projection in the form of a ball undetachably on the bearing cage, for example. On the other hand, they can serve to connect the two bearing cage parts.

According to a further preferred embodiment of the invention it can be provided that the needle bearing comprises at least one retaining element for securing the bearing needles on the bearing cage. For example, if recesses on the bearing cage for the bearing needles are open towards the longitudinal axis of the needle bearing, so that the bearing needles could fall out of the bearing cage in the direction of the longitudinal axis, this specifically can be prevented by the at least one retaining element.

It is favourable if the at least one retaining element defines a part of an inner bearing cage wall, beyond which the bearing needles project in radial direction pointing towards the longitudinal axis of the needle bearing. Thus, the bearing needles can be held on the bearing cage by the at least one retaining element and still perform their function as bearing elements for the drive shaft at the same time.

The instrument can be produced particularly simply and inexpensively if the at least one retaining element defines a sleeve section, which extends over at least 180° in peripheral direction. For example, the sleeve section can be formed from a thin metal sheet, which in particular can have incisions or recesses, through which the bearing needles can extend at least partially to come into contact with the drive shaft.

It is favourable if two retaining elements are provided. In particular, these can be configured identically. Naturally, it would also be conceivable to provide two or more retaining elements. However, in particular when the bearing cage is configured from two identical bearing cage parts, it is advantageous if only two retaining elements are provided that are respectively associated with one of the two bearing cage parts or are configured to be connected thereto.

In particular, it is advantageous to configure the retaining elements identically. A production expenditure of the instrument can thus be further minimised.

To prevent the at least one retaining element from detaching from the bearing cage in an undesirable manner, it is advantageous if the instrument comprises a coupling device for coupling the at least one retaining element and the bearing cage.

The coupling device can be configured in a particularly simple manner if it comprises first and second coupling elements, which are arranged or configured on the bearing cage on one side and on the at least one retaining element on the other side and which are in engagement with one another in a coupling position.

An assembly of the bearing cage can be simplified in particular by first coupling elements on the at least one retaining element being movable into the coupling position from an insertion position, in which the at least one retaining element can be inserted into the bearing cage. Thus, the at least one retaining element can be inserted into the bearing cage in a simple manner in order to secure the bearing needles on this, and can then be moved from the insertion position into the coupling position.

The bearing cage is preferably made from a metal or a plastic. In particular, this can be a sterilisable material. In the case of the metal it can be a corrosion-resistant steel in particular. The plastic can be a steam-sterilisable plastic, for example, i.e. polyether ether ketone (PEEK) or polytetrafluoroethylene (PTFE) in particular.

To improve the corrosion resistance of the needle bearing overall, it is favourable if the bearing needles and/or the locking elements are made from a metal. They are preferably made from a corrosion-resistant steel. However, they can also be formed from a hard metal.

It is advantageous if the bearing needles and/or the locking elements are made from a ceramic. In particular, a highly wear-resistant radial bearing can thus be formed.

In order to minimise the wear of parts abutting one another, it is favourable if the bearing needles or the locking elements are provided with a hard material coating. In particular, the hard material coating can be applied to corrosion-resistant steel or to a hard metal.

Hard material coatings that contain a metal nitride are particularly favourable. It is advantageous in particular to provide titanium nitride or chromium nitride as hard material coatings that contain these nitrides.

The invention further relates to a surgical handpiece comprising a drive arranged in a housing and a surgical instrument, wherein said surgical instrument is one of the above-described surgical instruments.

Such a handpiece then has the advantages described above in association with preferred embodiments of surgical instruments.

In particular, the handpiece and the instrument can be detachably connected to one another to thus use the handpiece multiple times even if the surgical instrument is only provided as a disposable instrument.

The present invention relates to a surgical drive system comprising at least one surgical handpiece with a drive arranged in a housing and an open-loop and/or closed-loop control device for open-loop and/or closed-loop control of the drive, further comprising at least one surgical instrument, said at least one surgical instrument is one of the above-described surgical instruments.

Such a drive system then has the advantages described above in association with preferred embodiments of surgical instruments.

FIG. 7 schematically shows a surgical drive system given the overall reference 10 and comprising an open-loop and/or closed-loop control arrangement in the form of a control device 12, five handpieces 14a to 14e, two shaver handpieces 16a and 16b, a gun handpiece 18, two supply lines in the form of connection cables 20 and 22 and also a pedal control 24. All the mentioned handpieces comprise an integrated electric motor as drive and thus form drive units.

The control device 12 comprises a flat screen 28 in the form of a touchscreen arranged in a housing 26. Three operating elements 30a to 30c or 30d to 30f are respectively arranged on both sides of the screen 28.

Two switches 32a and 32b are arranged in a line under the screen 28 with a port 34 for connecting the pedal control 24 by means of an optional connection cable 25 and with two ports 36a and 36b for connecting the connection cable 20 and 22, with which the handpieces can be connected to the control device 12.

Moreover, a connection 38 for a fluid system for the supply and removal of fluids from an operating area can be optionally provided, e.g. also for the supply of flushing or suction channels on gear units or tools (not shown), which can be connected to the handpieces 14, the shaver handpieces 16 or the gun handpiece 18 and together with which the handpieces form surgical instruments of the drive system 10.

The handpieces 14a to 14e respectively comprise a cable coupling 40a to 40e, which can be connected to a coupling piece 44 of the connection cable 20 or a coupling piece 46 of the connection cable 22, as desired. Similarly, the two shaver handpieces 16a and 16b and also the gun handpiece 18 respectively have a cable coupling 40f, 40g or 40h, which can be connected to one of the two coupling pieces 44 or 46.

At their respective other end the handpieces 14a to 14e are fitted with gear or tool couplings, which define tool coupling arrangements 42a to 42e, to which gear units (not shown) fitted, for example, with drills, saw blades or the like can be coupled and driven by the handpieces 14a to 14e. Depending on the configuration, the handpieces 14a to 14e can also be directly fitted with surgical instruments 15, e.g. milling cutters, drills or saw blades.

The handpieces 14a to 14e are preferably configured without sensors, i.e. they have no sensors to determine the rotational speed of the handpieces 14a to 14e during operation. The handpieces of the drive system 10 differ not only outwardly but also with respect to their internal structure, as shown schematically in FIG. 1. This means that the electric motors built into the handpieces 14a to 14e can be of different types and, for example, can differ in their parameters such as e.g. minimum speed, maximum speed, maximum current and maximum torque. Moreover, as in the case of the two shaver handpieces 16a and 16b, gears can be integrated that can also be optionally integrated into gear units, which can be coupled to the handpieces 14a to 14e and also to the gun handpiece 18. The gear units can also themselves be fitted with different surgical instruments 15 in the form of surgical tools, depending on the configuration.

Moreover, the shaver handpieces 16a and 16b respectively comprise a shaver coupling 48a or 48b for connection of a shaver attachment, e.g. for application in arthroscopy.

The connection cables 20 and 22 are provided for connecting to the control device with couplings 21 and 23, by means of which they connectable to the ports 36a and 36b.

The pedal control 24 connects to the control device 12 by means of a wireless data transmission system, e.g. by means of an infrared or radio transmission system. A connection of the pedal control 24 by means of a coupling piece 50 of the connection cable 25, which can be connected to the port 34, is also optionally possible. Two foot-operated switches 54a and 54b, by means of which in particular operation of the handpieces to the left or right can be controlled, are arranged on a housing 52 of the pedal control 24.

The gun handpiece 18 is fitted with two transducers 56, wherein the transducer 56a can be provided for activation of operation to the right of the motor and the transducer 56b for activation of an operation to the left of the motor.

The connection cables 20 and 22 differ in that in contrast to connection cable 20, connection cable 22 has an operating lever 58 provided thereon, with which an operator can activate a motor operation of a handpiece 14, a shaver handpiece 16 or the gun handpiece 18. The operating lever 58 has the function of a speed sensor, with which a rotational speed of the motor can be predetermined by an operator.

The structure of a surgical instrument 15 is shown schematically in FIG. 1. A proximal end of the instrument 15 is configured in the form of a coupling section 60, which can be coupled to a tool coupling arrangement 42 of the handpiece 14. The instrument 15 comprises an elongated hollow shank 62, which extends on the distal side of the tool coupling arrangement 42 and in which a drive shaft 64 is rotatably mounted. The shank 62 can be configured in several parts and, as in the exemplary embodiment represented in FIG. 1, can taper once or more times in outside diameter in the direction of a distal end 66. A distal shank section 68, which extends as far as the end 66, has a minimum outside diameter. In particular, this can be smaller than 5 mm.

For mounting the drive shaft 64 in the shank 62, two radial bearings in the form of ball bearings 70 and 72 are arranged offset in axial direction, i.e. in relation to a longitudinal axis 74 of the shank 62, slightly to the distal side of the coupling section 60 inside the shank 62. On the distal side of the ball bearing 72 still arranged in the proximal end region of the shank 62, the drive shaft 64 has a reduced outside diameter, which remains constant to beyond the end 66. A distal end of the drive shaft 64 forms a tool element 76, e.g. in the form of a ball-shaped cutter head 78, which is connected to the drive shaft 64 to be fixed against rotation or is configured in one piece with this.

A further ball bearing 80 that serves to mount the drive shaft 64 in the shank 62 is arranged inside the shank 62 slightly on the distal side of the ball bearing 72, but on the proximal side in relation to the transition to the shank section 68.

The shank section 68 can be relatively long, so that it is schematically shown in FIG. 1 as interrupted. As a result of this, high forces, in particular transverse forces in relation to the longitudinal axis 74, act on the tool element 76 and thus on the drive shaft 64 in the region of the distal end 66 during use of the instrument 15. To be able to absorb these forces with as low a friction as possible and to support the drive shaft 64 in relation to the shank 62, a further radial bearing 82 is provided slightly on the proximal side of the end 66 inside the shank 62, not in the form of a ball bearing, but in the form of a needle bearing 84. The needle bearing 84 is supported on the distal side against a ring surface 86, which faces in the proximal direction and is formed by a single-stage tapering of the inside diameter of the shank 62. On the proximal side the needle bearing 84 is supported against a further ring surface 88, which defines a distal end of a collet 90 inserted into the shank 62 and fixed in axial direction.

A structure of the needle bearing 84 is explained in more detail below in connection with FIGS. 3A to 3D.

The actual needle bearing 84 is axially secured to the shank by means of a needle bearing locking arrangement 92. The needle bearing locking arrangement 92 comprises first locking elements 94 and a second locking element 96 corresponding thereto. The locking elements 94, 96 are in engagement with one another transversely to the longitudinal axis 74 in a locking position. The first locking elements 94 are configured in the form of locking projections 98, which engage into a locking recess 100 defined by the second locking element 96. The locking projections 98 are configured in the form of balls 102 mounted to be freely rotatable, the locking recess 100 is configured in the form of an annular groove 104 corresponding in cross-section to the balls 102. The annular groove 104 is in turn configured on a sleeve-like holding ring 106, i.e. in an inside wall surface 108 thereof.

The balls 102 are held on a bearing cage 110 in locking element seatings 112 shaped specially for these. These are openings in the sleeve-like bearing cage 110 that taper approximately conically towards the longitudinal axis 74 in inner cross-section. By appropriate dimensioning of the locking element seatings 112 the balls 102 project over an outside face 114 of the bearing cage 110, but not over its inside face 116 running concentrically to the longitudinal axis 74.

The two locking element seatings 112 are configured diametrically opposed to one another, i.e. are offset 180° in peripheral direction, on the bearing cage 110. Three needle seatings 118 are respectively configured between the two locking element seatings 112 to receive a respective bearing needle 120. The needle seatings 118 are elongated hole-type openings of the bearing cage 110, the inner cross-section of which widens in radial direction with increasing distance from the longitudinal axis 74. The bearing needles 120 are configured in the form of solid cylinder bolts 122, which respectively have hemispherical ends 124 pointing away from one another. The needle seatings 118 are dimensioned so that the bearing needles 120 project slightly over the inside face 116 towards the longitudinal axis 74 and can thus come directly into contact with the drive shaft 64. This can then be supported not only in point form but also linearly, i.e. on all six bearing needles 120, in contrast to the case with ball bearings.

Three respective bearing needles 120 define a needle group 126. A spacing 128 between adjacent bearing needles 120 of a needle group 126 is smaller than a spacing 130 between two bearing needles 120 of adjacent needle groups 126. The balls 102 are configured on the bearing cage 110 in the region between the two needle groups 126.

The bearing cage 110 is formed in one piece, it being, however, sufficiently elastic that it can be deformed slightly for insertion after fitting with the balls 102 and also the bearing needles 120 for insertion into the holding ring 106 until the balls 102 engage into the annular groove 104. As soon as this is the case, the bearing cage 110 goes back into its original shape again and is thus axially secured to the shank 62 by means of the balls 102. To obtain the desired elasticity of the bearing cage 110, this is made from a material that is elastically deformable with corresponding dimensioning of the force application. In particular, the bearing cage 110 can be made from a plastic.

In the case of the needle bearing 84, the number of bearing needles 120 corresponds to an integral multiple of the number of both the first locking elements 94 and the second locking elements 96. In total, there are three-times as many bearing needles 120 as first locking elements and six-times as many bearing needles 120 as second locking elements 94.

Moreover, a minimum inside diameter 132 of the needle bearing 84 delimited by the bearing needles 120 corresponds to an outside diameter of the drive shaft 64 or, if need be, has the necessary play for this to allow as friction-free a rotation of the drive shaft 64 as possible in the shank 82.

A further exemplary embodiment of a needle bearing is shown schematically in FIGS. 4A to 4D and is given the overall reference 84a. It is axially secured to the shank 62 by means of the holding ring 106 in the manner described above.

The needle bearing 84a differs from the needle bearing 84 merely in the structure of the bearing cage 110a. Therefore, only those elements and parts in the case of needle bearing 84a that differ from needle bearing 84 are given identical references, but with the letter a added. This applies accordingly to the further exemplary embodiments also described below, in which references are provided with the letter b or c thereafter.

The number, arrangement and configuration of the bearing needles 120 and also the locking projections 98 in the case of needle bearing 84a are the same as those of needle bearing 84. There is merely a difference in the configuration of the locking element seatings 112a. These are delimited in peripheral direction by two holding members 134, which run parallel to one another and to the longitudinal axis 74 and have two bearing surfaces 136 inclined relative to one another for the balls 102. The holding members 134 are respectively separated in peripheral direction from a substantially cuboidal boundary projection 140 by a narrow slot 138 and are directed towards the respective other boundary projection 140. The holding members 134 can thus extend slightly in peripheral direction, as a result of which the slot 138 can widen slightly. This enables the balls 102 to be inserted into the locking element seating 112 in a simple manner.

The provision of the holding members 134 defining holding arms 142 enables the bearing cage 110 to be configured from a substantially inelastic material or to be so rigid that the bearing cage 110 cannot be inserted into the holding ring 106 with bearing needles 120 and balls 102 mounted thereon. To mount the needle bearing 84a in the holding ring 106 the bearing cage 110a is firstly fitted with bearing needles 120 and inserted into the holding ring 106. The balls 102 are then pressed from the inside against slide-on surfaces 144 of the holding arms 142 inclined relative to one another so that these spread slightly apart in peripheral direction and the balls 102 can slide into the locking element seatings 112. As soon as the balls 102 have passed through the opening delimited by the holding members 134 and the boundary projections 140, the holding members 134 can themselves pivot from their spread position, which is also referred to as the assembly position, back into their starting position again, as is shown schematically in FIG. 4D, for example. The last-mentioned position is also referred to as the locking position, in which the balls 102 are secured in the locking element seatings 112.

A further exemplary embodiment of a needle bearing is shown schematically in FIGS. 5A to 5E and is given the overall reference 84b. It is secured axially to the shank 62 by means of the holding ring 106 in the manner described above.

The needle bearing 84b differs from the needle bearing 84a only by the configuration of the bearing cage 110b. This is configured in two parts and comprises two identical bearing cage parts 146. Each bearing cage part 146 comprises a ring 148, which surrounds the longitudinal axis 74 concentrically. Six projections, of which four projections 150 are configured identically, respectively project from the ring 148 substantially parallel to the longitudinal axis 74. These respectively extend parallel to the longitudinal axis 74 over about a quarter of a total length of the bearing cage 110b. They respectively delimit needle seatings 118b. The projections 150 are respectively arranged in pairs, wherein a substantially cuboidal boundary projection 140b or 141b is formed between a respective pair of projections 150. The boundary projection 140b is separated by slots 138b from holding members 134b, which delimit a locking element seating 112b in peripheral direction.

Free ends of the holding members 134b configured in the form of holding arms 142b are configured in the form of first connection elements 152, which are formed on the boundary projection 141b to correspond to second connection elements 154. The first and second connection elements 152 and 154 form parts of a connection arrangement 156 for connecting the two bearing cage parts 146 to one another in a connection position. The first connection elements 152 are configured in the form of locking projections 158, which can engage into corresponding locking recesses 160, which are defined by the second connection elements 154, in the connection position. The locking projections 158 and the locking recesses 160 define respective edges, which run transversely to the longitudinal axis 74 and thus make it impossible for the bearing cage parts 146 to unintentionally detach from one another as a result of merely a tensile load applied parallel to the longitudinal axis 74.

The boundary projections 140b and 141b are arranged offset 180° relative to one another in peripheral direction, so that the first connection elements 152 of one bearing cage part 146 can be brought into engagement respectively with second connection elements 154 of the other bearing cage 146.

The bearing cage parts 146 can be formed to be substantially rigid and non-deformable except for holding arms 142b.

For assembly a bearing cage part 146 is inserted into the holding ring 106. The six bearing needles 120 and also the two balls 102 are placed into this bearing cage part 146. The second bearing cage part 146 is then pushed into the holding ring 106 from the other side until the locking projections 158 and locking recesses 160 forming a snap-in locking arrangement 162 mesh into one another and lock together. The bearing cage parts 146 then assume the connection position so that the bearing cage 110 is axially secured to the shank 62 by the holding ring 106 by means of the first locking elements 94 in the manner described above.

A further exemplary embodiment of a needle bearing is shown schematically in FIGS. 6A to 6F and given the overall reference 84c. It can be axially secured to the shank 62 in cooperation with the holding ring 106.

The needle bearing 84c comprises a bearing cage 110c, which is formed in one piece. It defines locking element seatings 112c respectively for a ball 102 and also needle seatings 118c respectively for one of the six bearing needles 120. Both the locking element seatings 112c and the needle seatings 118c widen substantially conically towards the longitudinal axis 74.

To prevent both the balls 102 and the bearing needles 120 from falling through or falling out in the direction of the longitudinal axis 74, two identical retaining elements 164 are provided. These are respectively formed from flat metal strips and form a section of a cylindrical sleeve. Moreover, the retaining elements 164 are configured symmetrically to a plane of symmetry containing the longitudinal axis 74. They comprise a middle strip 166, which overlaps from the inside the boundary projections 140c directed towards one another and thus also the locking element seating 112. In peripheral direction two webs 168, which respectively bear two retaining tabs 170, extend away from an end of the middle strip 166 in opposite directions. These respectively partially overlap one of the webs 172 laterally delimiting the needle seatings 118c in peripheral direction, but are slightly wider than these in peripheral direction, so that they laterally overlap the needle seatings 118 slightly just as the middle strips 166. They define openings 174 between them that are sufficiently narrow so that the bearing needles 120 cannot fall out of the needle seatings 118c in the direction of the longitudinal axis 74, but are securely held therein.

To undetachably secure the retaining elements 164 on the bearing cage 110c, a coupling device 180 given the overall reference 180 is provided, which comprises first coupling elements 176 on the retaining element 164 and second coupling elements 178 on the bearing cage 110c. The second coupling elements 178 are configured in the form of narrow recesses in the rings 148c on the ends of the bearing cage 110c. Two second coupling elements 178, which are formed offset 180° relative to one another in peripheral direction, are provided on each ring 148c.

The first coupling elements 176 are configured in the form of coupling tabs 182, which are directed away from one another in the axial direction and are movable from a starting position, in which they are directed substantially parallel to the longitudinal axis 74, into a coupling position, in which they protrude from free ends of the middle strip 166 in radial direction directed away from the longitudinal axis 74. They can be moved from the starting position into the coupling position by simple bending. A width of the coupling tabs 182 corresponds approximately to a width of the recesses forming the second coupling elements 178.

For assembly of the needle bearing 84c in the holding ring 106, the bearing cage 110c is firstly fitted with the two balls 102 and also the six bearing needles 120 and inserted into the holding ring. To secure the balls 102 and the bearing needles 120 against falling out, the retaining elements 164 produced with non-deformed coupling tabs 182 are inserted into the bearing cage 110 from opposite sides and offset 180° relative to one another. As soon as the retaining elements 164 assume their end position, the coupling tabs 182 are bent over so that they respectively engage into the second coupling elements 178 and thus axially secure the retaining elements 164 to the bearing cage 110c.

The bearing cages 110, 110a, 110b and 110c can be selectively made from a metal or from a plastic. The bearing needles 120 and also the balls 102 are selectively made from a metal, preferably from a hard metal, or a ceramic. Bearing needles 120 or balls 102 made from metal are preferably provided with a hard material coating. This can be a coating containing a metal nitride, in particular titanium nitride or chromium nitride, or composed of the specified materials.

What is claimed is:

1. A surgical instrument, comprising:
a shank,
a drive shaft, which is rotatably mounted in the shank and bears or comprises a tool element at a distal end,
a radial bearing arranged or configured in a distal end region of the shank for the rotatable mounting of the drive shaft on the shank, wherein the radial bearing being configured in the form of a needle bearing having a bearing cage, and
a needle bearing locking arrangement for axially securing the needle bearing on the shank, the needle bearing locking arrangement comprising at least one first locking element and at least one second locking element, one of the at least one first and second locking elements being arranged or held on the needle bearing, the other of the at least one first and second locking elements being arranged or held on the shank, and the at least one first locking element and the at least one second locking element being in engagement with one another in a locking position,
wherein:
the bearing cage defines a longitudinal axis and comprises an inner surface concentrically surrounding the longitudinal axis and an outer surface concentrically surrounding the longitudinal axis, and
the at least one first locking element protrudes from the outer surface or projects beyond the outer surface, but does not protrude from or project beyond the inner surface.

2. Surgical instrument according to claim 1, wherein a plurality of bearing needles are rotatably mounted in the bearing cage parallel to a longitudinal axis of the needle bearing.

3. Surgical instrument according to claim 2, wherein at least two of the bearing needles define a needle group and the needle bearing comprises at least two needle groups.

4. Surgical instrument according to claim 1, wherein:
the at least one first locking element is configured in the form of a locking projection,
the at least one second locking element is configured in the form of a locking recess, and
the locking projection and the locking recess are in engagement with one another in the locking position.

5. Surgical instrument according to claim 1, wherein the locking recess is formed on a holding ring, which is secured axially and non-rotatably to the shank.

6. Surgical instrument according to claim 1, wherein the at least one first locking element comprises a locking projection arranged or configured on the bearing cage between two bearing needles.

7. Surgical instrument according to claim 1, wherein the at least one first locking element comprises a locking projection arranged or configured on the bearing cage between two needle groups.

8. Surgical instrument according to claim 1, wherein the at least one first locking element comprises at least two locking projections.

9. Surgical instrument according to claim 2, wherein a minimum inside diameter of the needle bearing delimited by the bearing needles corresponds to an outside diameter of the drive shaft.

10. Surgical instrument according to claim 1, wherein the bearing cage is formed in one piece.

11. Surgical instrument according to claim 1, wherein the bearing cage is made from an at least partially elastic material.

12. Surgical instrument according to claim 1, wherein for each first locking element the bearing cage comprises a corresponding locking element seating, in which the first locking element is held with a holding member.

13. Surgical instrument according to claim 12, wherein the holding member is movable from an assembly position, in which the first locking element can be inserted into the corresponding locking element seating, into a locking position in which the first locking element is undetachably held on the bearing cage.

14. Surgical instrument according to claim 1, wherein the bearing cage comprises two interconnected bearing cage parts.

15. Surgical instrument according to claim 14, further comprising a connection device for connecting the two bearing cage parts.

16. Surgical instrument according to claim 15, wherein the connection device comprises first and second connection elements, which are respectively arranged or formed on one of the two bearing cage parts, which first and second connection elements are disengaged in a separation position and are in engagement with one another in a connection position.

17. Surgical instrument according to claim 2, wherein the needle bearing comprises at least one retaining element for securing the bearing needles on the bearing cage.

18. Surgical instrument according to claim 17, wherein the at least one retaining element defines a part of an inner bearing cage wall, beyond which the bearing needles project in a radial direction pointing towards the longitudinal axis of the needle bearing.

19. Surgical instrument according to claim 17, wherein the at least one retaining element defines a sleeve section, which extends over at least 180° in a peripheral direction.

20. Surgical instrument according to claim 17, further comprising a coupling device for coupling the at least one retaining element and the bearing cage.

21. Surgical instrument according to claim 1, wherein the bearing cage is made from a metal or a plastic.

22. Surgical handpiece, comprising:
a drive arranged in a housing, and
a surgical instrument, said surgical instrument comprising:
a shank,
a drive shaft, which is rotatably mounted in the shank and bears or comprises a tool element at a distal end,
a radial bearing arranged or configured in a distal end region of the shank a for the rotatable mounting of the drive shaft on the shank, the radial bearing being configured in the form of a needle bearing having a bearing cage, and
a needle bearing locking arrangement for axially securing the needle bearing on the shank, the needle bearing locking arrangement comprising at least one first locking element and at least one second locking element, one of the at least one first and second locking elements being arranged or held on the needle bearing, the other of the at least one first and second locking elements being arranged or held on the shank, and the at least one first locking element and the at least one second locking element being in engagement with one another in a locking position,
wherein:
the bearing cage defines a longitudinal axis and comprises an inner surface concentrically surrounding the longitudinal axis and an outer surface concentrically surrounding the longitudinal axis, and
the at least one first locking element protrudes from the outer surface or projects beyond the outer surface, but does not protrude from or project beyond the inner surface.

23. Surgical drive system, comprising:
at least one surgical handpiece with a drive arranged in a housing and at least one of an open-loop and closed-loop control device for at least one of open-loop and closed-loop control of the drive, and
at least one surgical instrument, said at least one surgical instrument comprising:
a shank, and
a drive shaft, which is rotatably mounted in the shank and bears or comprises a tool element at a distal end,
a radial bearing arranged or configured in a distal end region of the shank for the rotatable mounting of the drive shaft on the shank, the radial bearing being configured in the form of a needle bearing having a bearing cage, and
a needle bearing locking arrangement for axially securing the needle bearing on the shank, the needle bearing locking arrangement comprising at least one first locking element and at least one second locking element, one of the at least one first and second locking elements being arranged or held on the needle bearing, the other of the at least one first and second locking elements being arranged or held on the shank, and the at least one first locking element and the at least one second locking element being in engagement with one another in a locking position,
wherein:
the bearing cage defines a longitudinal axis and comprises an inner surface concentrically surrounding the longitudinal axis and an outer surface concentrically surrounding the longitudinal axis, and
the at least one first locking element protrudes from the outer surface or projects beyond the outer surface, but does not protrude from or project beyond the inner surface.

* * * * *